US006774616B2

United States Patent
Huhn et al.

(10) Patent No.: US 6,774,616 B2
(45) Date of Patent: Aug. 10, 2004

(54) SYSTEM FOR DETECTING FLUIDS IN A MICROFLUIDIC COMPONENT

(75) Inventors: Rüdiger Huhn, Lübeck (DE); Dietmar Sander, Hamburg (DE); Andreas Graff, Hamburg (DE); Lutz Timmann, Bad Bramstedt (DE)

(73) Assignee: Eppendorf AG, Hamburg (DE)

( * ) Notice: Subject to any disclaimer, the term of this patent is extended or adjusted under 35 U.S.C. 154(b) by 0 days.

(21) Appl. No.: 10/086,774

(22) Filed: Mar. 1, 2002

(65) Prior Publication Data

US 2002/0145121 A1 Oct. 10, 2002

(30) Foreign Application Priority Data

Apr. 4, 2001 (DE) .......................................... 101 16 674

(51) Int. Cl.[7] .......................... G01R 31/00; G01R 27/22
(52) U.S. Cl. ......................... 324/96; 324/92; 324/158.1
(58) Field of Search .............................. 417/36; 324/96, 324/158.1, 92; 422/55, 82.03, 82.05

(56) References Cited

U.S. PATENT DOCUMENTS 6,540,895 B1 * 4/2003 Spence et al. .............. 204/450

FOREIGN PATENT DOCUMENTS

| DE | 3243839 | 5/1984 |
| DE | 4305924 | 1/1994 |

* cited by examiner

Primary Examiner—N. Le
Assistant Examiner—Donald M Lair
(74) Attorney, Agent, or Firm—Sidley Austin Brown & Wood, LLP

(57) ABSTRACT

A system for detecting fluids in a microfluidic component having at least one microchannel including a limitation wall which has two surfaces which, facing the microchannel in a transparent area, are inclined towards each other at an acute angle, with the system further including a photo transmitter and a photo receiver which are disposed outside the component and are directed to the inclined surfaces in the transparent area of the limitation wall in such a way that if a gas is waiting in the microchannel on the two surfaces, a light ray emitted by the photo transmitter impinges on the photo receiver following a total reflection on the two surfaces and, if a liquid is waiting in the microchannel, the light ray enters the microchannel on at least one of the two surfaces and, as a result, the incidence of light into the photo receiver is reduced or prohibited.

18 Claims, 1 Drawing Sheet

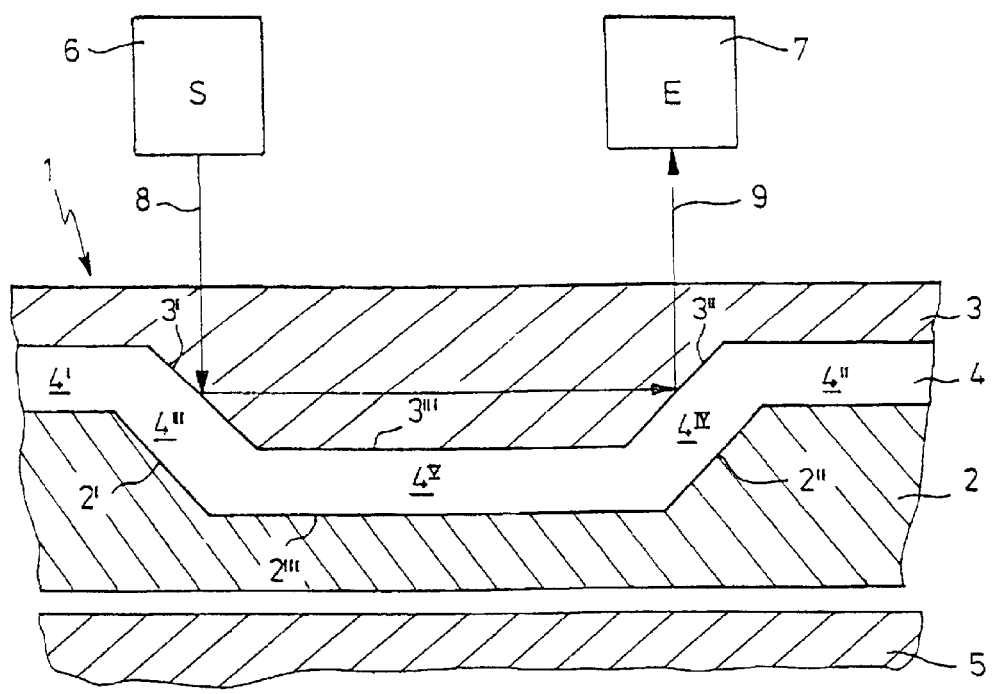

SYSTEM FOR DETECTING FLUIDS IN A MICROFLUIDIC COMPONENT

BACKGROUND OF THE INVENTION

1. Field of the Invention

The invention relates to a system for detecting fluids in a microfluidic component.

2. Description of the Prior Art

Microfluidic components in the sense of this application are components having at least one microchannel for storing and/or carrying fluids, i.e. liquids and/or gases. The microchannels can also be referred to as capillary microchannels. In addition, these microfluidic components may have more microstructures such as micropumps, microactors, microsensors, etc. Microfluidic components feature characteristic cross dimensions of the microchannels (e.g. the diameter or hydraulic diameter or the width and height) of about 1,500 µm as a maximum (preferably about 500 µm as a maximum) and about 5 µm as a minimum (preferably about 10 µm as a minimum). The microchannels may also be called capillary microchannels. The characteristic dimensions of further microstructures may also be found in the aforementioned ranges. In particular, these may be manufactured from semiconductors and/or plastics and/or glass and/or ceramics and/or metals where appropriate manufacturing techniques of the microsystem technology or microstructuring may be employed, e.g. lithography and etching processes (for semiconductors) or LIGA processes (for metals, plastics, and ceramics).

The degrees of filling by a fluid or the degree of emptying cannot be readily checked in microfluidic components, although this would be desirable in many cases. Thus, for instance, it would be helpful to know the degree of filling or that of emptying a microproportioning system in order to avoid faulty proportioning. Shocks acting on a microfluidic component might produce gas bubbles which can lead to malfunctions of the microfluidic component.

WO 99/10099 describes various microproportioning systems which comprise an open-jet proportioner or a micro-diaphragm pump. One of these microproportioning systems has a reservoir, a micro-diaphragm pump the inlet of which is connected to the reservoir, a proportioning aperture connected to the exit of the micro-diaphragm pump, and a proportioning control which is in an operative communication with the micro-diaphragm pump with the micro-diaphragm pump and the reservoir being combined in a microsystem technology or hybrid technology to form a component exchangeably connected to an actuation module. The pro-portioning control controls the volume to be pro-portioned via the stroke volume of the micro-diaphragm pump. To adjust an initial position for the displacement of the liquid column, the proportioning control is further connected to a sensor for detecting the meniscus of the liquid at the beginning of a displacement length of the liquid. The sensor is associated with a delivery tube for the liquid. In the first proportioning step, the micro-diaphragm pump pumps liquid out of the reservoir until the sensor detects the meniscus and, thus, reaches a defined zero position. After this, the volume to be proportioned is controlled via the known stroke volume of the micro-diaphragm pump. In further proportioning operations, the proportioning control may proceed on the assumption that the liquid column is waiting at the end of the delivery tube. This micropropor-tioning system establishes readiness for pro-portioning only at the beginning of the operation. Since the volume to be pro-portioned is controlled via the known stroke volume faulty proportioning might occur if the micro-diaphragm pump delivers air inclusions or the reservoir is exhausted.

Furthermore, it is problematic to detect the moving interface between liquid and gaseous transparent media by means of the optical sensor. Optical measurement is impaired, in particular, by the scattering and refraction effects and the small signal level swing. Measurement is restricted to detecting the interface and cannot differentiate whether liquid or air is just waiting at the sensor.

Therefore, it is the object of the invention to provide a system for detecting fluids in a microfluidic component which delivers a more favourable measuring signal and allows to differentiate between liquids and gases.

SUMMARY OF THE INVENTION

This and other object of the present invention, which will become apparent hereinafter, are achieve by providing a system for detecting fluids in a microfluidic component having the following features:

The microfluidic component has at least one microchannel including a limitation wall which has two surfaces which, facing the microchannel in a transparent area, are inclined towards each other at an acute angle, a photo transmitter and a photo receiver which are disposed outside the component are directed to the inclined surfaces in the transparent area of the limitation wall in such a way that if a gas is waiting in the micro-channel on the two surfaces a light ray emitted by the photo transmitter impinges on the photo receiver following a total reflection on the two surfaces and, if a liquid is waiting in the microchannel, enters the microchannel on at least one of the two surfaces and, as a result, the incidence of light into the photo receiver is reduced or prohibited.

The invention makes use of the fact that a critical angle dependent on the refractive indices of the two media exists at the boundary from an optically denser medium to an optically thinner medium so that a light ray incident in the denser medium onto the boundary with the thinner medium the angle of incidence of which exceeds the critical angle is completely reflected from this boundary (total reflection). It further utilizes the fact that the critical angle while transiting from a transparent solid body (e.g. of a plastic or glass) to air or another gas will be smaller than is the critical angle while transiting to a liquid. Therefore, the photo transmitter and the photo receiver are oriented to the surfaces of the transparent area of the limitation wall which are inclined towards each other at an acute angle, i.e. those of the optically denser area, in such a way that if a gas is waiting on the two surfaces total reflection will occur and the light ray will completely pass into the photo receiver. At this stage, the inclination of the surfaces towards each other ensures that the reflected air ray passes from one surface to the other. If a liquid is waiting on at least one of the surfaces the light ray enters the microchannel so that the photo receiver measures a light signal which is considerably reduced, or measures none at all. As a result, the inventive system can determine whether a gas or a liquid is waiting on the surfaces and, in addition, it can determine whether an interface existing between a gas and a liquid is migrating past the surfaces. The fact that the microchannel or capillary microchannel has very small cross dimensions causes a uniform meniscus to form between the liquid and the gas and neither droplets nor air bubbles that could adulterate the result to develop on the inclined surfaces. The limitation wall can be made of a plastic or glass, specifically in the transparent area in which there are the surfaces inclined towards each other at an acute angle.

Any carry-over of liquid through the photo transmitter and the photo receiver is ruled out because these are separated by the limitation wall from the microchannel. In addition, the design is simple because the photo transmitter and the photo receiver are oriented next to each other from one side to the surfaces inclined towards each other. The system has a distinct signal level swing and is very reliable.

In the area defined by the inclined surfaces, the microchannel may also be designed correspondingly thin as in areas adjoining it so that the fluids are conducted to the measuring range under favourable preconditions. According to an advantageous aspect, it is of a substantially constant cross-section in the area of the inclined surfaces and in areas adjoining them. According to another aspect, this is achieved for the surfaces inclined towards each other by the fact that the limitation wall disposed opposite the limitation wall having the inclined surfaces has surfaces which are substantial parallel thereto, at least in the areas opposite the inclined surfaces and in the areas adjoining them.

According to another aspect, the limitation wall disposed opposite the limitation wall having the inclined surfaces absorbs light at least in the areas opposite the inclined surfaces in order to suppress perturbing light reflections.

According to another aspect, the angle between the two surfaces is about 80 to 100°, preferably about 90°. Then, the photo transmitter and the photo receiver can be oriented, with their light axes, approximately in parallel and at an angle of incidence of about 45° to the respective inclined areas associated therewith.

According to another aspect, the component has a plurality of superposed walls. These can be designed so as to be planar substantially on either side with a limitation wall of the microchannel being adapted to have the inclined surfaces on a projection (e.g. of a prismatic shape) and the opposed limitation wall of the microchannel to have a receptacle accommodating the projection. The microchannel may be exclusively formed in the wall accommodating the projection and may be covered by the wall having the projection or may have portions complementing each other to form the microchannel in either wall.

According to another advantageous aspect, the photo transmitter and the photo receiver are designed in a single component, which is an advantage for their accommodation, assembly, and orientation.

According to another aspect, the photo transmitter and the photo receiver are separated from the microfluidic component, which favors the exchangeable nature of the microfluidic component and, in particular, its design as a disposable.

The photo transmitter and the photo receiver may operate, in particular, in the range of visible light. According to an aspect, they operate in the infrared range. The transparent area of the component will then be transparent to infrared radiation.

According to another aspect, the system is integrated in an apparatus to which the component is detachably connected. This makes it possible to exchange the component against another component after use. Preferably, the microfluidic component is a disposable, i.e. a component which is not employed again after use, but is discarded. In particular, the apparatus can have a receptacle for inserting the component. It can further have a detachable locked connection and/or interlocked connection and/or magnetic connection to the microfluidic component.

According to a further favourable aspect, the apparatus, on the side of the microfluidic component which is disposed opposite the side including the photo transmitter and the photo receiver, has a wall with specific reflection characteristics which, if no microfluidic component exists, has the consequence of a specific light incidence of the light originating from the photo transmitter into the photo receiver, which differs from the light incidence that occurs if a microfluidic component exists. Apart from detecting a gas or liquid in a component, this allows to detect whether the component exists at all in the apparatus.

According to another aspect, the apparatus is a hand-held apparatus.

The microfluidic component concerned may particularly be a cartridge of a microproportioning system, e.g. a cartridge of an enzyme proportioner as is described in WO 99/10099.

According to another aspect of the invention, the microfluidic component is a proportioning component, an analytical chip, a PCR component, a clean-up component, a liquid-conveying component, a component for capillary electrophoresis or a rectification column component.

A proportioning component generally serves for metering and providing one or more liquid volumes (or liquid aliquots) as exactly as possible.

An analytical chip is a component having a reaction chamber(s), detection structures, inlet and/or outlet ports, and fluidic communications. Also here, detecting the level of filling with liquid is of interest.

A PCR component serves for receiving, purposefully tempering, and routing along a sample containing nucleic acid with the aim being to amplify the DNA.

A clean-up component serves for selectively separating specific molecules from a sample, e.g. by bonding to surfaces, mechanical filters or chemical separation (elution).

A liquid-conveying component serves for actively conveying a liquid (e.g. via a pressure differential) or passively conveying it (e.g. via the capillary effect).

A component for capillary electrophoresis serves for spatially splitting up molecules according to their size (chain length) with the movement of the molecules being caused by a differential of the electric potential.

A rectification column component serves for spatially splitting up molecules according to bond characteristics with the movement of the molecules being adapted to be accomplished by the pressure differential or capillarity.

Finally, an aspect of the invention provides that if a gas and/or liquid is detected an evaluation device coupled to the photo receiver initiates an output and/or a turn-on or turn-off of the apparatus and/or a function of the apparatus.

BRIEF DESCRIPTION OF THE DRAWINGS

The invention will now be explained with reference to the accompanying drawing which shows the system in a vertical partial section through a microfluidic component.

DETAILED DESCRIPTION OF THE PREFERED EMBODIMENT

The microfluidic component 1 has a basic body 2 onto which a lid 3 is placed. A microchannel 4 or capillary microchannel is formed between the basic body 2 and the lid 3 so that the basic body 2 and the lid 3 define limitation walls for the microchannel 4.

The microchannel 4 extends in two lateral portions 4', 4" substantially in parallel with the outer surfaces of the basic body 2 and the lid 3. In an intermediate region, it has two portions 4''', 4$^{IV}$ inclined towards each other at an acute angle between which, in turn, a portion 4$^V$ is disposed which extends substantially in parallel with the outer surfaces. The portions 4''' and 4$^{IV}$ of the microchannel 4 are oriented approximately at an angle of 45° from the outer surfaces of the basic body 2 and the lid 3. The cross-section of the microchannel 4 is substantially constant.

The inclined portions 4''', 4$^{IV}$ of the microchannel 4, on the side of the lid 3, are defined by two surfaces 3', 3" which are inclined approximately at an angle of 45° towards the lid plane and approximately at an angle of 90° towards each other. The basic body 2 has surfaces 2', 2" which are in parallel with these surfaces 3', 3". Between the surfaces 3', 3", the lid has a surface 3''' parallel to the lid plane, and parallel to which surface the basic body 2 has a surface 2'''.

In the example, the basic body 2 is of a substantially planar design with its upper surface having worked therein the microchannel 4 and an indentation having the surfaces 2', 2", 2'''.

The lid 3 is also substantially planar, but has the surfaces 3', 3", 3''' on a prism-shaped elevation. The elevation engages the indentation and the adjoining planar surfaces of the lid 3 cover the adjoining portions 4', 4" of the duct.

The lid 3 is designed transparent in the area which is adjacent to the portions 4''', 4$^{IV}$, and 4$^V$ of the microchannel 4. It can also be designed so as to be non-transparent in the portions which 4" of the microchannel 4.

The basic body 2 is designed to be absorbent at least in its areas below the transparent region of the lid 3, i.e. in the surfaces 2', 2" and the intermediate region 2'''.

The component 1 including the basic body 2 and the lid 3 is disposed on a partially reflective substrate 5.

A photo transmitter 6 and a photo receiver 7 having parallel light axes 8, 9 are disposed on the opposite side. The light axis 8 of the photo transmitter 6 is oriented onto the inclined surface 3' and the light axis 9 of the photo receiver 7 is oriented onto the inclined area 3", i.e. at an angle of incidence of 45° each.

This system is adapted to detect the presence or absence of a liquid below the surfaces 3', 3". If there is air on the surfaces 3', 3" in the microchannel 4 the light ray is led by a double total reflection into the photo receiver 7 from the photo transmitter 6 as is depicted in the drawing.

If a liquid is waiting on one of the two surfaces 3', 3" the light will pre-dominantly propagate in the microchannel 4, which prohibits total reflection more or less and a distinct change of the signal may be established on the photo receiver 7.

If there is no component 1 above the substrate 5 the light ray emitted by the photo transmitter 6 is partially reflected into the photo receiver 7 with the evaluation of the signal delivered by the photo receiver 7 allowing to determine that reflection has been effected on the substrate. This makes it possible to detect the non-existence of the component 1 above the substrate 5.

What is claimed is:

1. A system for detecting fluids in a microfluidic component (1) having the following features:
   The microfluidic component (1) has at least one microchannel (4) including a limitation wall (3) which has two surfaces (3', 3") which, facing the microchannel (4) in a transparent area, are inclined towards each other at an acute angle,
   a photo transmitter (6) and a photo receiver (7) which are disposed outside the component (1) are directed to the inclined surfaces (3', 3") in the transparent area of the limitation wall (3) in such a way that if a gas is waiting in the microchannel (4) on the two surfaces (3', 3") a light ray emitted by the photo transmitter (6) impinges on the photo receiver (7) following a total reflection on the two surfaces (3', 3") and, if a liquid is waiting in the microchannel (4), enters the microchannel (4) on at least one of the two surfaces (3', 3") and, as a result, the incidence of light into the photo receiver (7) is reduced or prohibited.

2. The system according to claim 1, wherein the microchannel (4) is of a substantially constant cross-section at least in the area of the inclined surfaces (3', 3") and in the areas adjoining them.

3. The system according to claim 1, wherein the limitation wall (2) disposed opposite the limitation wall (3) having the inclined surfaces (3', 3") has substantially parallel upper and lower limitations walls (2', 2") at least in the areas opposite the inclined surfaces (3', 3") and in the areas adjoining them.

4. The system according to claim 1, wherein the limitation wall (2) disposed opposite the limitation wall (3) having the inclined surfaces (3', 3") absorbs light at least in the areas disposed opposite the inclined surfaces.

5. The system according to claim 1, wherein the angle between the two surfaces (3', 3") is about 80 to 90°.

6. The system according to claim 1, wherein the component (1) has a plurality of superposed walls (2, 3).

7. The system according to claim 1, wherein the photo transmitter (6) and the photo receiver (7) are designed in a single component.

8. The system according to claim 1, wherein the photo transmitter (6) and the photo receiver (7) are separated from the microfluidic component (1).

9. The system according to claim 1, wherein the photo transmitter (6) and the photo receiver (7) operate in the infrared range.

10. The system according to claim 1, which is integrated in an apparatus to which the microfluidic component (1) is detachably connected.

11. The system according to claim 10, wherein the microfluidic component (1) is inserted in a receptacle of the apparatus.

12. The system according to claim 10, wherein the apparatus has a detachable locked connection and/or interlocked connection and/or magnetic connection to the microfluidic component (1).

13. The system according to claim 10, wherein the apparatus is a handheld apparatus.

14. The system according to claim 1, wherein the microfluidic component (1) is a disposable.

15. The system according to claim 1, wherein the apparatus, on the side of the microfluidic component (1) which is disposed opposite the side including the photo transmitter (6) and the photo receiver (7), has a wall (5) with specific reflection characteristics which, if no microfluidic component (1) exists, results in a specific light incidence of the light originating from the photo transmitter (6) into the photo receiver (7), which differs from the light incidence which occurs if a microfluidic component (1) exists.

16. The system according to claim 1, wherein the microfluidic component (1) is a cartridge of a microproportioning system.

17. The system according to claim 1, wherein the microfluidic component (1) is a proportioning component, an analytical chip, a PCR component, a clean-up component, a liquid-conveying component, a component for capillary electrophoresis or a rectification column component.

18. The system according to claim 1, wherein an evaluation device initiates a detection of a gas and/or liquid of a delivery device and/or a turn-on or turn-off of an apparatus and/or a function of the apparatus.

* * * * *